(12) United States Patent
Niizato et al.

(10) Patent No.: US 6,440,951 B1
(45) Date of Patent: Aug. 27, 2002

(54) METHOD FOR TREATMENT OF DIABETES

(75) Inventors: Tetsutaro Niizato; Masaharu Shiotani; Yoko Shoji, all of Yokohama (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 09/991,650

(22) Filed: Nov. 26, 2001

Related U.S. Application Data

(62) Division of application No. 09/509,664, filed as application No. PCT/JP98/04470 on Oct. 2, 1998.

(30) Foreign Application Priority Data

Oct. 3, 1997 (JP) .............................................. 9-271205

(51) Int. Cl.$^7$ ............................................... A61K 31/66
(52) U.S. Cl. ...................................... 514/110; 514/866
(58) Field of Search ................................. 514/110, 866

(56) References Cited

U.S. PATENT DOCUMENTS 4,943,629 A * 7/1990 DeVries et al. ............. 536/117

* cited by examiner

Primary Examiner—Kevin E. Weddington
(74) Attorney, Agent, or Firm—Larson & Taylor PLC

(57) ABSTRACT

Fosfomycin or a pharmaceutically acceptable salt thereof has been found to have an action of lowering the serum glucose level and is recognized to be useful as an orally administrable remedy for treating diabetes. It has further been found that the serum glucose level-lowering action of fosfomycin or its salt can be enhanced synergistically and significantly when forfomycin is administered in association with vanadyl sulfate and the like. Therefore,the composition comprising fosfomycin or its salt and vanadyl sulfate or the like is useful as an orally administrable remedy for treating diabetes.

1 Claim, No Drawings

METHOD FOR TREATMENT OF DIABETES

This application is a division of Ser. No. 09/509,664 filed Mar. 31, 2000, which is a 371 of PCT/JP98/04470 filed Oct. 2, 1998.

TECHNICAL FIELD

This invention relates to a novel composition for therapeutically treating diabetes, which comprises as an active ingredient fosfomycin, a known antibiotic, or a pharmaceutically acceptable salt thereof. This invention also relates to a novel composition for therapeutically treating diabetes, which comprises fosfomycin or a pharmaceutically acceptable salt thereof and also a vanadyl compound (or a vanadyl salt) containing vanadyl group ($VO^{2+}$) as active ingredients. This invention further relates to a novel method for treating diabetes by administration of fosfomycin or a salt thereof.

Furthermore, this invention includes the use of fosfomycin or a salt thereof or the use of a mixture of fosfomycin or a salt thereof with a vanadyl compound, in the preparation of a remedy of diabetes.

BACKGROUND ART

Diabetes are one of typical diseases incident to old adults, similarly to cancers, brain infarction, cardiac infarction, Alzheimer's disease and the like. There are numerous latent diabetes, too. Diabetes are diseases caused by occurrence of abnormal metabolisms of glucose, protein and lipid due to a deficiency or insufficiency of the actions of insulin. Typical signs of diabetes include an abnormal increase in the serum glucose level over the normal range of the glucose level and an excretion of glucose in the urine.

Insulin is one of hormones in pancreas and has such functions to promote the permeability of glucose through the cell membranes in liver, muscles and adipose tissues and thereby to increase the uptake of glucose by the cells, and further to promote the combustion of glucose in the glycolysis step and oxidation step of glucose in the muscles and also to elevate the activity of the enzyme system for synthesizing glycogen from glucose. It is known that by exhibiting the above biological functions, insulin has such action "in vivo" as to keep the serum glucose level at the normal levels.

In 1985, the classification of diabetes was proposed by The World Health organization (WHO). Diabetes are classified into two large groups, namely, the insulin-dependent diabetes mellitus (Type I, IDDM) where the patients do not-produce insulin; and the non-insulin-dependent diabetes mellitus (Type II, NIDDM) where the patients cause an insulin resistance. For the treatment of the type II diabetes, some orally administrable remedies are used. Under the present situation, however, the treatment of the type I diabetes has to resort on the injection of insulin. It has therefore been required worldwide to develope such novel oral remedies which are effective for treating the diabetes by oral administration.

It has been known from about 1960's that "ouabain" which has a digitalis-like cardiac action is effective as a strong inhibitor to Na,K-ATPase. Further, ouabain is known to have an insulin-like action in view of the fact that the action of inhibiting Na, K-ATPase can participate in the transportation and metabolism of glucose "in vivo". In 1977, Cantley et al, found that sodium orthovanadate which is a penta-valent vanadium compound and which was accidentally mixed in ATP can strongly inhibit Na,K-ATPase (L. C. Cantley et al., "J.Biol.Chem." Vol. 252, No.21, 7421–7423 (1977)). Judging from the fact that ouabain inhibits Na,K-ATPase and possesses the insulin-like action, many researchers then anticipated that the penta-valent vanadium compound, which was already admitted as an inhibitor to Na,K-ATPase similarly to ouabain, would also exhibit the insulin-like action (refer to Hiroshi Sakurai, "Gendai Kagaku" Current Chemistry in English, Jul. 14–20, 1996). As a result of many subsequent researches relating to the action of penta-valent vanadium on the uptake of glucose into cells, there is reported that some vanadates which are penta-valent vanadium compounds possess the insulin-like actions (see, for example, Degani et al, "Biochemistry" Vol.20, p.5795 (1981)).

Further, streptozotocin is known to be an antibiotic which is produced by actinimycetes. It is known that streptozotocin, if administered to animals, can specifically destroy β-cells of the islets of Langerhans in pancreas to stop the secretion of insulin and thus involve occurrence of experimental diabetes in the animals. In 1985, Heyliger et al, reported that when the diabatic rats which were made diabatic by administration of streptozotocin (abbreviated as STZ), namely the rats called as STZ diabatic rats, are given sodium metha-vanadate ($NaVO_3$) in the form of an aqueous saline solution as drinking water, the so treated rats showed such a decrease in the glucose level in blood serum that the glucose level was returned to the normal level at 6th week after the administration of the vanadate. Heylinger et al also reported that a vanadate showed the insulin-like action with respect to the glucose metabolism (see C. B. Heyliger et al., "Science" Vol.27, p.1474–1477 (1985)).

Further, Japanese Patent Application Laid Open Publication, KOKAI-Hei 2-292217 specification (issued on Dec. 3, 1990) discloses that several vanadium complexes of the following formulae(A)~(G) possess a function of lowering the serum glucose level and that vanadyl sulfate ($VOSO_4$) also possesses the function of lowering the serum glucose level.

Vanadium (VI) complex having the following formula (A)

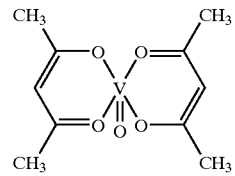

(A)

Salicylaldehyde-vanadium (VI) complex having the following formula (B)

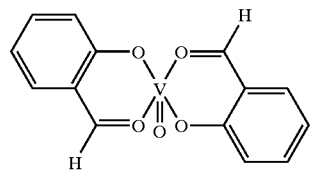

(B)

Gluconic acid- or L-lactic acid-vanadium (VI) complex having the following formula (C)

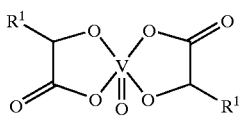

wherein R¹ stands for a group —CH(OH)CH(OH)CH(OH)CH₂ OH, or a methyl group.

L-Cystein methyl ester- or L-cysteamine-vanadium (VI) complex having the following formula (D)

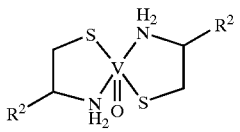

wherein R² stands for a hydrogen atom or a methoxycarbonyl group.

L-(+)-Tartaric acid-vanadium (VI) complex having the following formula (E)

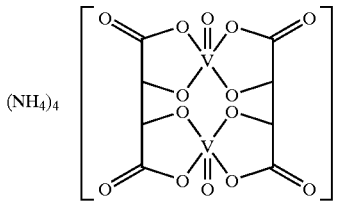

Oxalic acid-vanadium (VI) complex having the following formula (F)

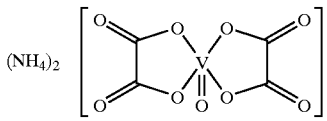

Malonic acid-vanadium (VI) complex having the following formula (G)

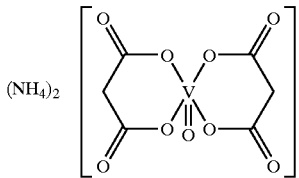

While, Hiroshi Sakurai et al, report that vanadyl sulfate possesses the action of lowering the serum glucose level, and they report that comparisons are made between various vanadium compounds, including vanadium oxide, metavanadic acid, orthovanadic acid, vanadyl sulfate, potassium vanadate, sodium vanadate and the like, with remarking that the toxicity of sodium metavanadate ($NaVO_3$) which is a penta-valent vanadium compound, when orally administered, was about 10 times higher than the toxicity of vanadyl sulfate($VOSO_4$) which is a tetra-valent vanadium compound (see Hiroshi Sakurai et al, "Trace Elements in vivo" published by Hirokawa Book Company, 1994).

Up to date, there have been synthesized a variety of vanadium compounds which are of a low toxicity and are orally administrable. Peroxo-vanadium compounds thus synthesized were studied on their function of lowering the serum glucose level, and further investigations were made to estimate whether a combined use of the penta-valent vanadium compounds synthesized and hydrogen peroxide can give rise to a synergistic effect on the action of lowering the serum glucose level. However, there is found no report to show that said combined use would have any synergistic effect in the action of lowering the serum glucose level (see B. I. Poner et al., "J.Biol.Chem." , vol.269, No.6, 4596–4604 (1994)).

Specifically, fosfomycin is a known antibiotic having an antibiotic activity. Fosfomycin or a pharmaceutically acceptable salt thereof has the structure represented by the following general formula (I)

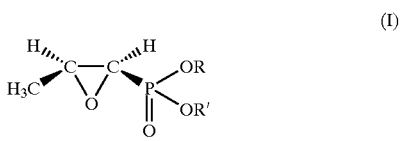

wherein R and R' are each a hydrogen atom or a pharmaceutically acceptable monovalent metal atom, for example, an alkali metal atom, preferably sodium, potassium or ammonium radical, or R and R' are combined together to show a divalent metal atom pharmaceutically acceptable, for example, an alkaline earth metal atom, preferably calcium or magnesium.

Fosfomycin and a salt thereof are useful as an antibiological agent and are also useful as a relieving or preventing agent for nephro-toxicity of aminoglycoside antibiotics (see Japanese Patent Publication Sho-64-5574) and are further useful as an agent for reducing the adverse side-effects of anticancer agents (Japanese Patent Publication Hei-5-2649). As far as we, the inventors of this invention know, however, such fact has never been known that fosfomycin has any action for lowering the serum glucose level of the diabetic rats.

DISCLOSURE OF THE INVENTION

An object of this invention is to provide a novel remedy for treating diabetes, which is capable of administering either orally or parenterally. Another object of this invention is to provide such a novel, orally administrable drug preparation for treating diabetes, which contains as an active ingredient a vanadium compound having an action capable of lowering an unusually high serum glucose level by the diabetes to the normal serum glucose level, and which further contains as another active ingredient such a second compound capable of enhancing the action of lowering the serum glucose level shown by the said vanadium compound and also possessing by itself the action of lowering the serum glucose level. A further object of this invention is to provide a novel method for treating diabetes. Other objects of this invention will become apparent from the undermentioned explanation.

We, the inventors of this invention, have made extensive investigations in order to achieve the objects of this invention as above-mentioned. As a part of our investigations, we have first carried out experimental studies on the oral administration of vanadyl sulfate [molecular formula VOSO$_4$; called also as vanadium oxysulfate (VI)] to the STZ diabetic rats which were experimentally induced by the administration of streptozotocin (STZ) (hereinafter sometimes abbreviated as "STZ diabetic rats"). Said vanadyl sulfate used here is already known to possess the action capable of lowering such an unusually high serum glucose level of the experimental diabetic rats to the normal serum glucose level. Our experimental studies in question have now been made to estimate how the dosage of vanadyl sulfate orally administered can influence on the strength of the action of vanadyl sulfate for lowering the serum glucose level, the strength of the action thereof for lowering the urea type nitrogen level in the serum, the strength of the action thereof for lowering the creatinine level in the serum etc., as well as on the strength of the action thereof for lowering the urinary glucose (urinary sugar) level, the strength of the action thereof for lowering the urinary total protein level, and the strength of the action thereof for lowering the urinary creatinine level. Then, we have further proceeded our experimental studies to carry out the oral administration of vanadyl sulfate in combination with various additional compounds to the STZ diabetic rats, in order to detect what are such certain compounds which can exhibit a synergistically enhancing effect on the serum glucose level-lowering action of vanadyl sulfate.

As a result of these investigations, we have found for the first time that when disodium salt or calcium salt of fosfomycin is administered orally to the STZ diabetic rats, it can show such activity that the fosfomycin salt does not exhibit any action of lowering the serum glucose level at a low dosage of administration of it, but it can exhibit a significant action of lowering the serum glucose level at a high dosage of administration of it, even when it is administered by itself. Thus, we have now found, quite unexpectedly, that fosfomycin or a pharmaceutically acceptable salt thereof, only when administered at a high dosage, can have the action of lowering the serum glucose level and then is useful as a remedy for treating diabetes.

Furthermore, we have now found that fosfomycin or a salt thereof possesses such a function that fosfomycin or its salt is capable of synergistically enhancing the action of lowering the serum glucose level as shown by the vanadyl, sulfate which is exhibited upon the administration of vanadyl sulfate to the STZ diabetic rats. We have further found that as similar as the vanadyl sulfate, vanadyl dichloride (VI) of formula VOCl$_2$ and vanadyl dibromide (VI) of formula VOBr$_2$ are also expectable to have the action of lowering the serum glucose level, and also that fosfomycin or a salt thereof is expectable to be able to enhance the serum glucose level-lowering action of vanadyl dichloride and vanadyl dibromide. This invention has been completed on the basis of these findings.

According to a first aspect of this invention, therefore, there is provided a composition for treating diabetes, which comprises as an active ingredient fosfomycin or a pharmaceutically acceptable salt thereof, in combination with a pharmaceutically acceptable solid or liquid carrier or carriers for the active ingredient.

In the composition for treating diabetes according to the first aspect of this invention, fosfomycin may preferably be in the form of its salt, and it may suitably be in the form of monosodium salt or disodium salt or calcium salt. The toxicity of fosfomycin itself is extremely low (see Japanese Journal of Antibiotics, January, 1979). Fosfomycin or its salt may be orally administered, and the dosage of fosfomycin for the oral administration may be in the range of 0.05–5 g/day. Fosfomycin or its salt may also be parenterally administered. The parenteral administration may be effected by intravenous administration, intramuscular or subcutaneous injection, intraperitoneal administration, intrarectal administration, percutaneous administration or intramucosal administration.

In the composition according to the first aspect of this invention, the carrier to be incorporated may be any of solid or liquid carriers conventionally used in the art. The solid carrier may, for example, be starch, Lactose, crystalline cellulose and calcium phosphate. The liquid carrier may, for example, be water, aqueous common salt solution and ethanol. The content of fosfomycin as active ingredient in the composition of this invention may, for example, be in the range of 5–80% based on the total weight of the composition. The composition according to the first aspect of this invention may be formulated in the form of a preparation suitable for oral administration or parenteral administration.

In general, the composition according to the first aspect of this invention may be formulated in the form of usual preparations. The preparations may additionally contain one or more of filler, extender, binder, moistening agent, disintegrator, surface active agent and lubricant. The preparations may be in the form of tablets, pills, powder, liquid, suspension, emulsion, granules, capsules, suppository, injection (solution or suspension) or ointment. When the composition is prepared in the form of tablets, there may be incorporated therein as the carrier a solid carrier such as lactose, sodium chloride, starch, calcium carbonate, kaolin, crystalline cellulose, silica, etc.; a binder such as water, ethanol, propanol, simple syrup, starch liquor, gelatin solution, carboxymethyl cellulose, shellac, methyl cellulose, potassium phosphate, polyvinylpyrrolidone, etc.; a disintegrator such as dry starch, sodium alginate, agar powder, laminaran powder, sodium hydrogen carbonate, polyoxyethylene sorbitan fatty acid esters, sodium lauryl sulfate, stearic acid monoglyceride, etc.; a disintegration inhibitor such as stearin, cacao butter, hydrogenated oil, etc.; an absorption promotor such as quaternary ammonium salts, sodium lauryl sulfate, etc.; a humectant such as glycerin, starch, etc.; an adsorbent such as bentonite, colloidal silica, etc.; and a lubricant such as purified talc, stearic acid salts, boric acid powder, polyethyleneglycol, etc. If necessary, tablets may also take a form of tablets coated with a usual coating, for example, sugar-coated tablets, gelatin-coated tablets, film-coated tablets or two-layered or multi-layered tablets.

In cases where the composition according to the first aspect of this invention is prepared in the form of pills, there may be incorporated as the carrier an excipient such as lactose, starch, cacao butter, hydrogenated vegetable oils, kaolin, talc, etc.; a binder such as powdery gum arabic, powdery tragacanth, gelatin, ethanol, etc.; a disintegrator such as laminaran, agar, etc. In cases where the composition is prepared in the form of suppositories, there may be incorporated as the carrier polyethyleneglycol, cacao butter, higher alcohols, higher alcohol esters, gelatin, semi-synthesized glycerides, etc.

When the composition according to the first aspect of this invention is used as a preparation for oral administration, it is preferred to formulate the composition in the form of tablets, pills, granules, etc. by incorporating known pharmaceutically acceptable excipient(s), for example, lactose, crystalline cellulose, starch, calcium phosphate; binder(s), for example, starch, sodiumcaramelose, hydroxypropyl cellulose; disintegrator, for example, calcium caramelose, calcium carbonate; lubricant(s), for example, magnesium stearate, talc, etc. It is also possible to formulate the composition in the form of a dry syrup or a syrup in a usual manner. Further, by applying a known retarted release formulation technique to these various types of preparations, there may be formulated a sustained preparation.

Other types of the preparations include sublingual tablet, suppository, collunarium, ophthalmic solution or endermic absorbent preparation in the form of plaster, ointment or cream.

In cases where the composition of this invention is in the form of orally administrable preparations, sublingual tablets or suppository, fosfomycin or its salt of general formula (I) may be administered at a daily dosage of 0.05–5 g, preferably 0.1–1 g, once a day or twice or three times a day dividedly. For the other preparation forms, the dosage of fosfomycin may suitably vary depending upon the purpose of treatment.

In cases where the composition according to the first aspect of this invention is formulated in the form of capsules, the capsules are prepared by mixing the active ingredient with various carriers as exemplified above and by filling the mixture in hard gelatin capsules or soft capsules. Further, when the composition is formulated in the form of injections, it is preferred that the composition is first prepared in the form of liquid, emulsion or suspension, which is then sterilized and is made isotonic with blood. When the composition is formulated in the form of injections, there may be incorporated as the diluent water, aqueous lactic acid solution, ethyl alcohol, propylene glycol or polyoxyethylene sorbitan fatty acid esters. In this case, common salt or glycerin may be added to the injections in an amount sufficient to give an isotonic solution. Further, there may be added solubilizer, buffering agent or antipaining agent which is conventionally used.

When the composition according to the first aspect of this invention is orally administered for the purpose of treating diabetes, fosfomycin disodium salt as the active ingredient may be orally administered consecutively. The consecutive administration may be effected for 2–30 days, preferably for 5 days, and it may dividedly be made in two or three times a day. The dose of fosfomycin disodium salt is 32–3000 mg/kg, preferably 320–1000 mg/kg. We have found that oral administration of fosfomycin disodium salt at a dose of 160 mg/kg showed a tendency to improve the serum glucose level in blood. We have further confirmed that the oral administration of fosfomycin disodium salt or calcium salt at a dose of 320 mg/kg twice a day for 5 consecutive days can evidently ameliorate an unusually high serum glucose level or some other symptoms of diabetes mullitus to get a good effect of the treatment of diabetes.

Further, according to a second aspect of this invention, there is provided a method for treating diabetic patient, which comprises administering orally or parenterally to the patient who shows a symptom of unusually high serum glucose level, an amount of fosfomycin or a pharmaceutically acceptable salt thereof in an effective dose to lower the serum glucose level in blood.

According to a third aspect of this invention, there is provided the use of fosfomycin or a pharmaceutically acceptable salt thereof, in the preparation of a composition for treating diabetes.

Further, according to a fourth aspect of this invention, there is provided a composition for treating diabetes, which comprises fosfomycin or a pharmaceutically acceptable salt thereof as a first active ingredient, and a vanadyl compound (or a vanadyl salt) represented by the following general formula (II)

$$O=V(X)_n \tag{II}$$

wherein V stands for tetravalent vanadium, X stands for a sulfate group —$SO_4$ or a chlorine atom or bromine atom, and n is 1 when X is the sulfate group —$SO_4$ and n is 2 when X is the chlorine or bromine atom, as a second active ingredient, in combination with a pharmaceutically acceptable solid or liquid carrier or carriers for these active ingredients.

In the composition according to the fourth aspect of this invention, fosfomycin is preferably in the form of its disodium salt or calcium salt. The vanadyl compound of general formula (II) (i.e. vanadyl salt) is preferably vanadyl sulfate $VOSO_4$. The vanadyl sulfate may also be in the form of its tri-hydrate or tetra-hydrate.

Fosfomycin or its salt and the vanadyl compound of general formula (II), which are used as the active ingredients in the composition according to the fourth aspect of this invention, may be administered orally or parenterlly, similarly to the composition according to the first aspect of this invention. The carrier incorporated in this composition may be of the same kinds as those used in the composition according to the first aspect of this invention. Further, the composition according to the fourth aspect of this invention may be formulated in the form of orally or parenterally administrable preparations, similarly to the composition according to the first aspect of this invention.

When the composition of the fourth aspect of this invention is orally administered for the treatment of diabetes, fosfomycin disodium salt as an active ingredient may be administered for 2–30 consecutive days, preferably 5 consecutive days. In parallel therewith, vanadyl compound of formula (II) may also be administered consecutively. The single dose for oral administration of fosfomycin disodium salt is 32–3000 mg/kg, whereas the single oral dose of the vanadium compound of formula (II), particularly vanadyl sulfate, is 1–100 mg/kg. we have confirmed by our experiments that oral administration of fosfomycin sodium salt and vanadyl sulfate concurrently by the administration of the composition of the fourth aspect of this invention can remarkably ameliorate the various symptoms of diabetes, with involving a synergistic effect of the treatment over the single administration of fosfomycin by itself.

In the composition of the fourth aspect of this invention, it is preferable that fosfomycin or its salt and vanadyl compound of general formula (II) are contained in a molar ratio in the range of 1:0.01 to 1:10, preferably in the range of 1:0.1 to 1:3. The composition preferably contains fosfomycin disodium salt or calcium salt and also contains, as the vanadyl compound of general formula (II), vanadyl sulfate of formula $VOSO_4$, vanadyl dichloride of formula $VOCl_2$ or vanadyl dibromide of formula $VOBr_2$ or a hydrate thereof.

Further, according to a fifth aspect of this invention, there is provided a method for treating a diabetic patient, which comprises administering orally or parenterally to the patient who shows a symptom of an unusually high serum glucose level, a mixture of fosfomycin or pharmaceutically acceptable salt thereof with a vanadyl compound (or a vanadyl salt) represented by the following general formula (II)

$$O=V(X)_n \tag{II}$$

wherein V stands for tetravalent vanadium, X stands for a sulfate group —$SO_4$ or a chlorine atom or bromine atom, and n is 1 when X is the sulfate group —$SO_4$ and n is 2 when X is the chlorine or bromine atom or a hydrate thereof, in an effective dose of said mixture to lower the serum glucose level in the blood.

In the method according to the fifth aspect of this invention, fosfomycin disodium salt or calcium salt may be administered at a dosage of it effective to lower the serum glucose level, and also vanadyl sulfate $VOSO_4$ or vanadyl dichloride $VOCl_2$ or vanadyl dibromide $VOBr_2$ or a hydrate thereof may be administered at a dosage thereof effective to lower the serum glucose level. Further, it is preferred to set that the proportions of the fosfomycin salt and the vanadyl compound to be administered are corresponding to a molar ratio in the range of 1:0.01 to 1:10. In this method, fosfomycin or its salt and the vanadyl compound of general formula (II) or a hydrate thereof may be orally administered, simultaneously, for 2–30 consecutive days.

Furthermore, according to a sixth aspect of this invention, there is included the use of a mixture of fosfomycin or a pharmaceutically acceptable salt thereof with a vanadyl compound of general formula (II) hereinbefore defined or a hydrate thereof.

In addition, with respect to the toxicity, $LD_{50}$ value in rats of fosfomycin calcium salt is not lower than 3.5 g/kg at its oral administration and vanadyl sulfate showed no toxicity in rats at its oral administration of 50 mg/kg.

BEST MODE FOR CARRYING OUT THE INVENTION

This invention is now illustrated more concretely with reference to the following Examples.

EXAMPLE 1

In this Example, as animals to be tested, the STZ diabetic rats were prepared from normal Wistar rats having an average body weight of 250 g (male, 6 weeks of age). For this purpose, the normal Wistar rats were made diabetic by a single administration of a dose of 60 mg/kg of STZ intravenously. The normal Wistar rats (male) which are to be subjected to the STZ administration, when they were given 20 g/day of feed and 36 g/day of water, had have such body conditions that average values each of their urine volume output, serum glucose level, serum urea nitrogen level, serum creatinine level, serum total protein level and serum albumin level of the rats are amounting to 18 ml, 152 mg/dl, 18.0 mg/dl, 0.5 mg/dl, 5.63 g/dl and 4.2 g/dl, respectively.

The STZ diabetic rats as prepared and used in this Example are such those rats (7 weeks of age, 6 rats per group) which had received an intravenous administration of a single dose of 60 mg/kg of STZ and which were confirmed to have been made diabetic with their showing such symptom that their serum glucose level was not less than 400 (mg/dl), when measured by sampling their blood at 1 week lapse from the STZ administration. These STZ diabetic rats showed such disease symptoms which are characterized by unusually much increased values of their taken amounts of water and the urine volume output, serum glucose level and urinary glucose level, and which are also characterized by abnormal increase in the urea nitrogen (BUN)level and creatinine level in their serum, as well as an unusual decrease in the serum total protein level and an increase in the urinary creatinine level.

One week after the intravenous administration of single dose 60 mg/kg of STZ, to the male 7-week-old Wistar rats (6 rats per group), which have been confirmed to have the symptoms of diabetes, were orally administered either one or both of vanadyl sulfate $VOSO_4$ at a single dose of 50 mg/kg and fosfomycin disodium salt (abbreviated as FOM-Na) at a single dose of 160 mg/kg, twice a day for 5 consecutive days, by administration of the test compounds) in the form of the aqueous solutions. The body weight, amounts (volumes) of feed taken, water taken and urine volume output of the rats under test were measured with lapse of time. Further, sampling of blood from the rats was effected at a time of 24 hours after the final administration of the compound(s) tested. Samplings of the urine from the rats were effected over 12 hours after the final administration of the compound(s) tested, and the blood sample and the urine samples as collected were subjected to the following biochemical tests.

In the biological tests of the blood sample above-mentioned, there were measured the serum glucose level, serum urea nitrogen level, serum creatinine level, serum total protein level and serum albumin level. In the biochemical tests of the urine sample, there were measured the collected amounts of the glucose, total protein and creatinine present in the urine. As the animals to be used for control tests (untreated), there were used such male 7-week-old wistar rats (6 rats per group) which were made to be the STZ diabetic conditions, but which did not receive the administration of the test compounds). These rats for the comparative purpose were tested similarly to the above tests.

The measured values (average values) of the body weight, the volumes of feed taken and water taken and the urine volume output shown by the test rats are summarized in Table 1 below for exhibiting the general observation of the body conditions of the rats under test. The measured values (average values) of the biochemical tests of the serum (blood) sample are shown in Table 2 below. The measured values (average values) of the biochemical tests of the urine sample are shown in Table 3 below.

TABLE 1

| Test compound and its dose | Body weight (g) | | Feed volume taken (g) | | Water volume taken (g) | | Urine volume output (ml) | |
|---|---|---|---|---|---|---|---|---|
| The day of measurement (Day) | 0 | 5 | 0 | 5 | 0 | 5 | 0 | 5 |
| Control group (Untreated) | 239 ± 4 | 247 ± 7 | 35 ± 1 | 34 ± 3 | 115 ± 20 | 139 ± 15 | 115 ± 6 | 113 ± 11 |
| $VOSO_4$ 50 mg/kg | 226 ± 8 | 239 ± 9 | 35 ± 2 | 29 ± 4 | 140 ± 12 | 99 ± 24 | 111 ± 10 | 82 ± 21 |
| FOM-Na 160 mg/kg | 235 ± 4 | 282 ± 3 | 36 ± 1 | 37 ± 1 | 153 ± 5 | 142 ± 16 | 115 ± 5 | 106 ± 7 |
| FOM-Na 160 mg/kg + $VOSO_4$ 50 mg/kg | 237 ± 7 | 251 ± 7 | 35 ± 2 | 21 ± 5* | 139 ± 6 | 53 ± 11* | 110 ± 4 | 29 ± 9*# |

Mark* shows a significant difference of the measured value from the control group (untreated).
$P < 0.05$
Mark# shows a significant difference of the measured value from the treated rat group to which $VOSO_4$ alone was administered.
$P < 0.05$

TABLE 2

Biochemical Test of Serum sample

| Test compound and its dose | Glucose level (mg/dl) | | Urea nitrogen level (mg/dl) | Creatinine level (mg/dl) | Total protein level (g/dl) | Albumin level (g/dl) |
|---|---|---|---|---|---|---|
| The day of measurement (Day) | 0 | 5 | 5 | 5 | 5 | 5 |
| Control group (Untreated) | 418 ± 5 | 424 ± 22 | 30 ± 1 | 0.6 ± 0.02 | 5.2 ± 0.1 | 3.9 ± 0.1 |
| $VOSO_4$ 50 mg/kg | 416 ± 13 | 339 ± 70 | 23 ± 2 | 0.6 ± 0.02 | 5.2 ± 0.1 | 3.8 ± 0.1 |
| FOM-Na 160 mg/kg | 418 ± 16 | 365 ± 21 | 31 ± 2 | 0.6 ± 0.02 | 5.5 ± 0.1 | 4.2 ± 0.1*# |
| FOM-Na 160 mg/kg + $VOSO_4$ 50 mg/kg | 416 ± 15 | 175 ± 40*# | 20 ± 1* | 0.5 ± 0.02*# | 5.7 ± 0.1*# | 4.1 ± 0.1*# |

Mark* shows the significant difference from the control group (untreated).
$P < 0.05$
Mark# shows the significant difference from the treated rat group to which $VOSO_4$ alone was administered.
$P < 0.05$

TABLE 3

Biochemical Test of Urine sample

| Test compound and its dose | Glucose (g/12 hr) | | Total protein (g/12 hr) | | Creatinine (mg/12 hr) | |
|---|---|---|---|---|---|---|
| | The day of measurement (Day) | | | | | |
| | 0 | 5 | 0 | 5 | 0 | 5 |
| Control group (Untreated) | 8.8 ± 1.1 | 9.7 ± 2.1 | 4.5 ± 2.6 | 7.4 ± 3.8 | 11.3 ± 1.4 | 13.0 ± 0.9 |
| $VOSO_4$ 50 mg/kg | 9.1 ± 1.4 | 6.8 ± 3.2 | 7.2 ± 8.2 | 3.9 ± 0.8 | 12.5 ± 1.8 | 12.1 ± 2.5 |
| FOM-Na 160 mg/kg | 9.2 ± 0.9 | 8.9 ± 1.3 | 4.2 ± 1.1 | 5.6 ± 2.2 | 12.5 ± 0.7 | 12.5 ± 0.8 |
| FOM-Na 160 mg/kg + $VOSO_4$ 50 mg/kg | 8.9 ± 0.6 | 1.5 ± 2.1 ** ## | 4.4 ± 2.2 | 2.5 ± 1.4 * | 12.8 ± 1.3 | 8.4 ± 2.5 ** ## |

Mark* and mark** show the significant difference from the control group (untreated).
*: $P < 0.05$
**: $P < 0.01$
Mark# and mark## show the significant difference from the treated rat group to which $VOSO_4$ alone was administered.
: $P < 0.05$
: $P < 0.01$ As is clear from the test results shown in Table 1, Table 2 and Table 3 above, both of the single administration of fosfomycin disodium salt alone at a dose of 160 mg/kg and of the single administration of vanadyl sulfate alone at a dose of 50 mg/kg can evidently be shown to have the action of lowering an unusually high serum glucose level and urinary glucose level in the STZ diabetic rats under test. on the other hand, when fosfomycin disodium salt was administered in combination with vanadyl sulfate, there has been recognized that ameliorations can be achieved not only to remarkably decrease the abnormally high serum glucose level and high urinary glucose level, but also to lower the high urea nitrogen level and high creatinine level in the serum and to make better the reduced total protein level and reduced albumin level in the serum and also to suppress the high creatinine content in the urine.

EXAMPLE 2

To male Wistar 7-week-old rats (7 rats per group), which were intravenously administered with a single dose of 60 mg/kg of STZ and which were confirmed to have been made diabetic after the lapse of 1 week from the STZ administration, fosfomycin disodium salt or fosfomycin calcium salt (FOM-Ca) was orally administered at a dose of 320 mg/kg, twice a day for 5 consecutive days. Then, sample of the blood of each test rat was taken. and subjected to the biochemical tests. The test results obtained are shown in Table 4 below.

The test results of Table 4 indicate that fosfomycin disodium salt and fosfomycin calcium salt both can clearly ameliorate the symptoms of diabetes, particularly the unusually high serum glucose level. Thus, it has been confirmed that fosfomycin or its salt is effective for the therapeutic treatment of diabetes.

TABLE 4

| Test compound and its dose | Glucose (mg/dl) | | Triglyceride (mg/dl) | | Creatinine (mg/dl) | Total protein (g/dl) | Albumin (g/dl) |
|---|---|---|---|---|---|---|---|
| The day of measurement (Day) | 0 | 5 | 0 | 5 | 5 | 5 | 5 |
| Control group | 431 ± 8 | 413 ± 17 | 169 ± 29 | 115 ± 23 | 0.56 ± 0.02 | 4.89 ± 0.06 | 3.7 ± 0.0 |
| FOM-Na 320 mg/kg | 432 ± 6 | 345 ± 23* | 211 ± 30 | 65 ± 3 | 0.50 ± 0.00* | 5.26 ± 0.06* | 4.0 ± 0.1* |
| FOM-Ca 320 mg/kg | 431 ± 5 | 336 ± 23* | 178 ± 18 | 59 ± 7* | 0.51 ± 0.01 | 5.37 ± 0.07* | 4.1 ± 0.1* |

Mark* shows the significant difference from the control group.
$P < 0.05$

INDUSTRIAL APPLICABILITY

According to this invention, fosfomycin or its salt has been found to have an action capable of lowering the serum glucose level and to be effective as an orally administrable drug for treating the diabetes. Further, it has been recognized that the serum glucose level-lowering action of fosfomycin or its salt can be synergistically and remarkably enhanced, if it is administered in combination with vanadyl sulfate or its equivalent vanadyl compound. Therefore, a composition comprising fosfomycin or its salt in combination with vanadyl sulfate or its equivalent vanadyl compound is useful as an orally administrable drug for treating the diabetes.

What is claimed is:

1. A method for treating a diabetic patient, which comprises administering orally or parenterally to the patient who shows a symptom of an unusually high serum glucose level, an amount of fosfomycin or a pharmaceutically acceptable salt thereof in an effective dose to lower the serum glucose level in blood.

* * * * *